US00PP29781P3

(12) United States Plant Patent
Levan, Jr.

(10) Patent No.: US PP29,781 P3
(45) Date of Patent: Oct. 30, 2018

(54) ***LAGERSTROEMIA* PLANT NAMED 'LIPIPETZ'**

(50) Latin Name: ***Lagerstroemia indica* x *fauriei* hybrid**
Varietal Denomination: Lipipetz

(71) Applicant: David A. Levan, Jr., Coatesville, PA (US)

(72) Inventor: David A. Levan, Jr., Coatesville, PA (US)

( * ) Notice: Subject to any disclaimer, the term of this patent is extended or adjusted under 35 U.S.C. 154(b) by 38 days.

(21) Appl. No.: 15/530,760

(22) Filed: Feb. 23, 2017

(65) Prior Publication Data

US 2018/0242490 P1 Aug. 23, 2018

(51) Int. Cl.
*A01H 5/02* (2018.01)

(52) U.S. Cl.
USPC ..... Plt./252

(58) Field of Classification Search
USPC ..... Plt./226, 252
See application file for complete search history.

*Primary Examiner* — Keith O. Robinson
*Assistant Examiner* — Karen M Redden
(74) *Attorney, Agent, or Firm* — Samuel R. McCoy, Jr.

(57) ABSTRACT

A new and distinct *Lagerstroemia* cultivar named 'Lipipetz' which is characterized by the combination of a compact, freely-branching growth habit with a generally round shape, dense foliage, an abundance of pink flowers borne on terminal panicles from summer into early fall, and the stability of these characteristics from generation to generation.

4 Drawing Sheets

Latin name of the genus and species: The Latin name of the genus and species of the novel variety disclosed herein is *Lagerstroemia indica* x *fauriei* hybrid.

Variety denomination: The inventive cultivar of *Lagerstroemia* disclosed herein has been given the variety denomination 'Lipipetz'.

BACKGROUND OF THE INVENTION

Parentage: 'Lipipetz' is a seedling selection resulting from the open pollination of *Lagerstroemia* hybrid 'Hopi' (not patented) performed by the inventor at his commercial ornamental plant nursery in Coatesville, Pa. on Sep. 1, 2006. Having grown several varieties of *Lagerstroemia* that performed well in his climate, the inventor endeavored to develop new cultivars with favorable gene expression using one such cultivar, *Lagerstroemia* hybrid 'Hopi', as the seed parent. Mature 'Hopi' plants were grown in close proximity to a number of additional cultivars, to facilitate cross pollination. Seed was subsequently collected from these 'Hopi' plants, germinated, and the seedlings grown to a mature size in order to evaluate the progeny for unique characteristics which may be of commercial value. In September of 2008, one such seedling was observed to possess a more compact growth habit relative to the parent plant and other progeny plants. The plant was isolated for propagation and further evaluation and given the name, 'Lipipetz'.

Asexual Reproduction: Asexual reproduction of 'Lipipetz', by way of softwood stem cuttings, was first performed in June of 2009 in Coatesville, Pa. Through three subsequent generations, the unique features of this cultivar have proven to be stable and true to type.

SUMMARY OF THE INVENTION

The cultivar 'Lipipetz' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Lipipetz'. These characteristics in combination distinguish 'Lipipetz' as a new and distinct *Lagerstroemia* hybrid cultivar:

1. *Lagerstroemia* 'Lipipetz' exhibits a compact, freely-branching growth habit with dense foliage; and
2. *Lagerstroemia* 'Lipipetz' exhibits a generally round shape; and
3. *Lagerstroemia* 'Lipipetz' exhibits an abundance of pink flowers borne on terminal panicles from summer and into early fall, weather depending; and
4. *Lagerstroemia* 'Lipipetz' exhibits lateral branches with excellent cold hardiness.

BOTANICAL DESCRIPTION OF THE PLANT

Figure 1:
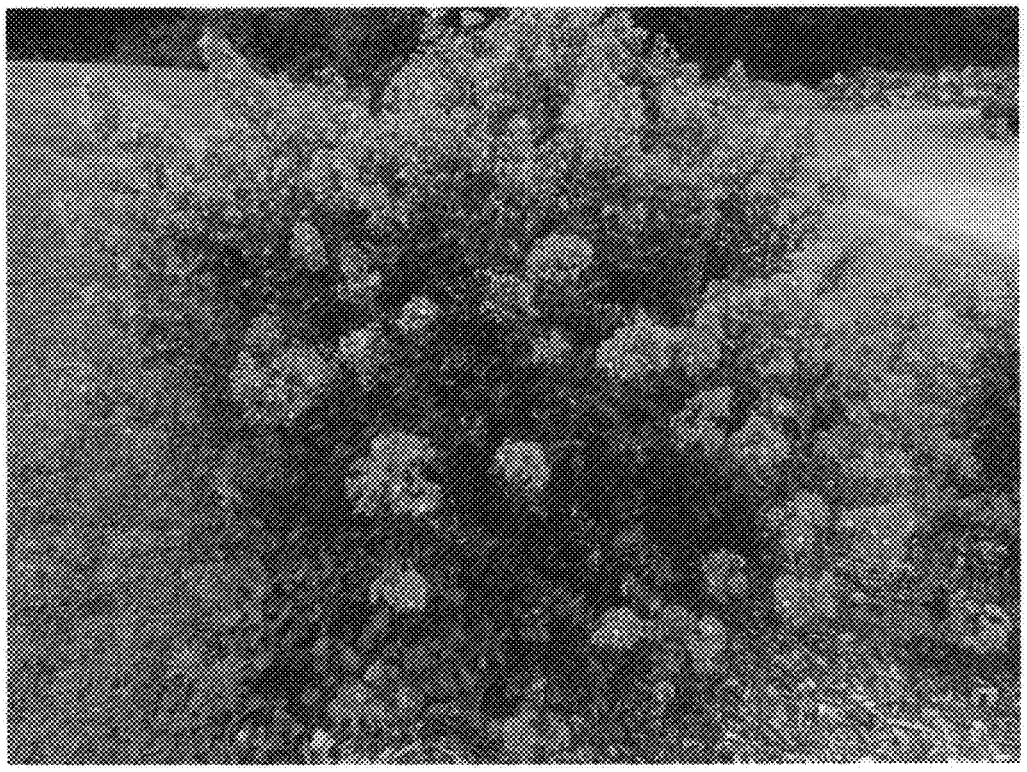
FIG. 1 illustrates, as nearly true as it is reasonably possible to make the same in color photographs of this type, the original 'Lipipetz' plant at approximately 10 years old, field-grown in Coatesville, Pa. The photograph was taken in late July and illustrates the summer bloom habit.
Figure 2:
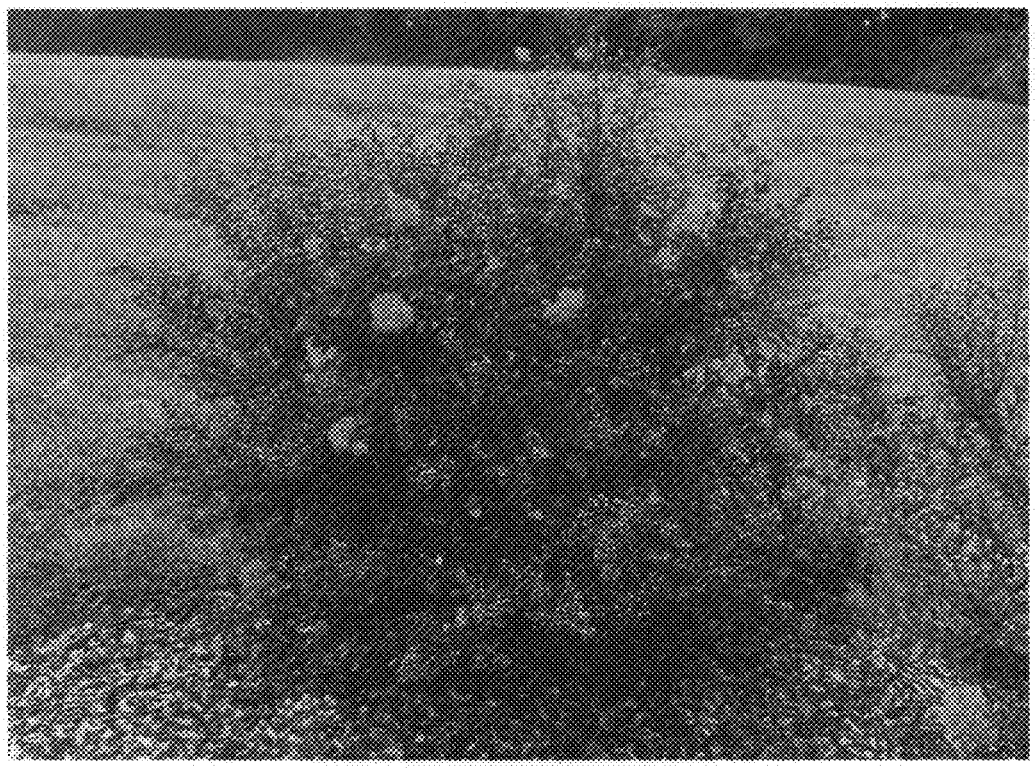
FIG. 2 illustrates, as nearly true as it is reasonably possible to make the same in color photographs of this type, the original 'Lipipetz' plant at approximately 9 years old, field-grown in Coatesville, Pa. The photograph was taken in mid-September and illustrates the continued blooming into late summer.
Figure 3:
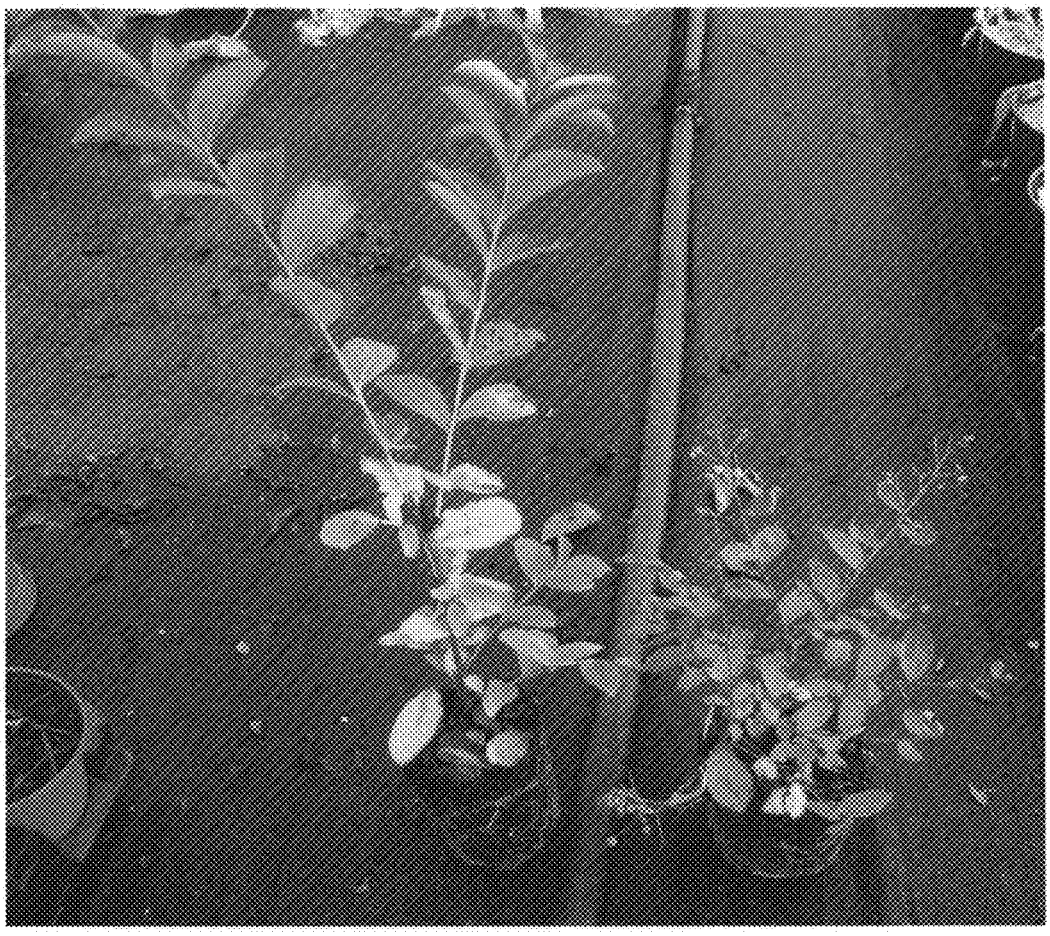
FIG. 3 illustrates, as nearly true as it is reasonably possible to make the same in color photographs of this type, a comparison of 'Lipipetz' (right) with the parent plant, 'Hopi' (left). Both plants were rooted in mist chamber in mid-June of 2016 and grown in a 3 inch nursery pots, in an unheated poly greenhouse, until time of photo on Nov. 30, 2016. Of note is the more compact growth habit of 'Lipipetz'.
Figure 4:
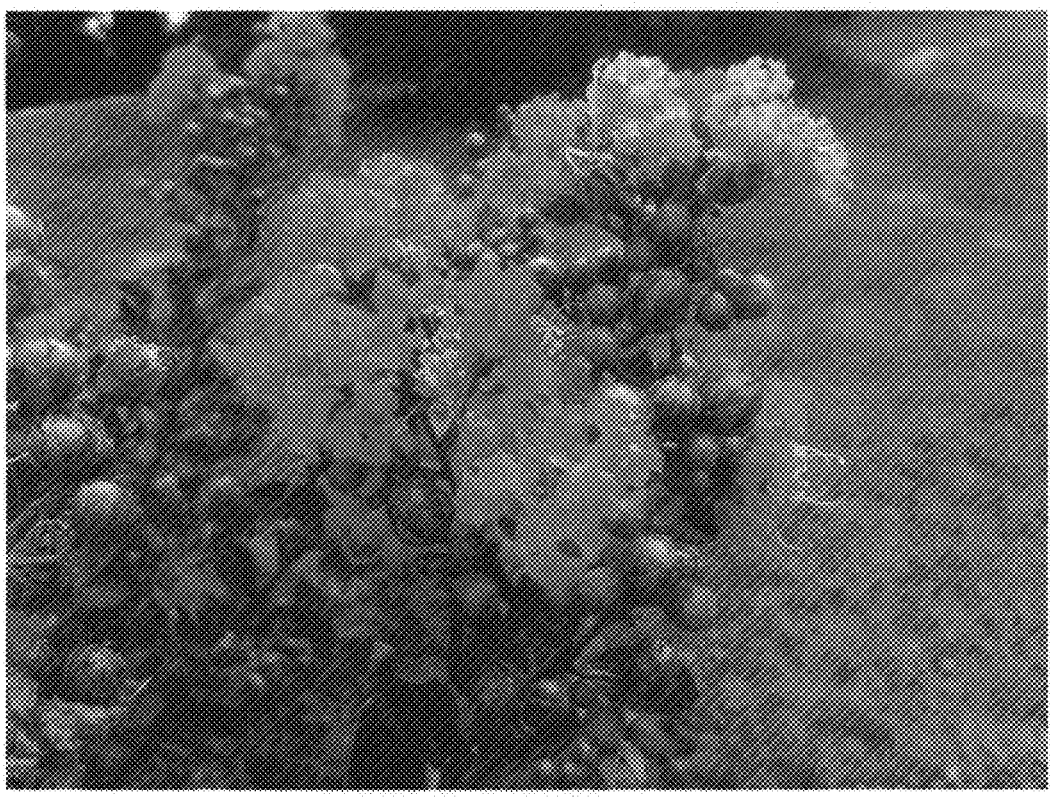
FIG. 4 illustrates, as nearly true as it is reasonably possible to make the same in color photographs of this type, an exemplary inflorescence of 'Lipipetz'.

The following observations and measurements made in November of 2016 and, unless otherwise indicated, describe a six month old potted 'Lipipetz' plant grown in a poly greenhouse in Coatesville, Pa. Those skilled in the art will appreciate that certain characteristics will vary with older or, conversely, with younger plants. 'Lipipetz' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'Lipipetz' and comparisons with the parent plants and most similar commercial *Lagerstroemia* cultivar known to the inventor are provided below.

Plant description:

*Growth habit*.—Perennial flowering shrub.

*Plant shape*.—Rounded.

*Average height*.—Approximately 125 cm when fully matured.

*Average width*.—Approximately 125 cm when fully matured.

*Plant vigor*.—Moderately vigorous.

*Propagation details*.—Asexual propagation may be accomplished by both softwood and hardwood stem cuttings.

*Time to initiate roots*.—Approximately 21 days are required to initiate roots from a softwood cutting; approximately 3 to 4 months are required for hardwood cuttings.

*Time to produce a marketable rooted cutting*.—Approximately 6 to 8 weeks when propagated in the spring.

*Time to produce a marketable* 1 *gallon potted plant*.—Approximately 12 months.

*Disease and pest resistance or susceptibility*.—Neither tolerance nor resistance to normal diseases and pests of *Lagerstroemia* have been observed.

*Environmental tolerances*.—Adapt to USDA Zones 5 to 11; drought resistant once established.

Root system:

*General*.—Fibrous; freely branched and moderately dense rooting.

*Distribution in the soil profile*.—Shallow to moderately deep.

Stems:

*Branching habit*.—One main stem, itself freely branching, and giving rise to numerous lateral branches.

*Aspect*.—Average angle is approximately 60 degrees from main stem.

*Cross section*.—Quadrangulate with small winged appendages approximately 0.5 mm tall.

*Strength*.—Strong.

*Length of lateral branches*.—22.5 cm.

*Diameter of lateral branches*.—Averaging 0.25 cm at the base.

*Internode length on lateral branches*.—Approximately 1.25 to 2.5 cm.

*Texture, pubescence and luster of lateral branches*.—Smooth, glabrous, and matte.

*Color, juvenile*.—A mixture of greyed-red, RHS 178A, and greyed-orange, RHS 176A.

*Color, mature*.—A mixture of yellow-green, RHS 152A, and greyed-brown; RHS 199A, 199B, and 199D.

*Color at internodes*.—Greyed-brown, RHS 199D.

*Bark*.—Exfoliating in stripes; color is brown, nearest to RHS 200B.

Foliage:

*Arrangement*.—Alternate.

*Attachment*.—Petiolate.

*Division*.—Simple.

*Number of leaves per lateral branch*.—24.

*Lamina*.—Dimensions — 4.6 cm long and 2.8 cm wide, on average. Shape — Ovate. Aspect — Involute. Apex — Bluntly acuminate. Base — Cuneate. Margin — Finely serrulate. Pubescence, adaxial surface — Glabrous. Texture and luster of adaxial surface — Smooth and moderately glossy. Pubescence, abaxial surface — Glabrous. Texture and luster of abaxial surface — Smooth and moderately glossy. Color — Juvenile foliage, adaxial surface — Yellow-green, nearest to RHS 146A, and finely margined greyed-red, RHS 178A. Juvenile foliage, abaxial surface — Yellow-green, RHS 146B, and suffused with greyed-red, RHS 178A, towards the margins and apex. Mature foliage, adaxial surface — In between yellow-green, RHS 147A, and green, RHS 137A. Mature foliage, abaxial surface — Yellow-green, nearest to RHS 146B. Venation — Pattern — Pinnate. Color, adaxial surface — Yellow-green, RHS 146A, and suffused with greyed-orange, RHS 176D, at the base and along the proximal one-third portion of the midrib. Color, abaxial surface — Yellow-green, RHS 146D, and suffused with greyed-orange, RHS 176B, at the base.

*Petiole*.—Length — 1.0 mm. Width — 1.25 mm. Texture — Glabrous; smooth. Luster — Moderately glossy. Strength — Strong. Color, adaxial surface — Yellow-green, RHS 146A, and suffused with greyed-orange, RHS 176D. Color, abaxial surface — Yellow-green, RHS 146D, and suffused with greyed-orange, RHS 176B.

Inflorescence:

*Type*.—Panicle.

*Natural flowering season*.—Late June through September in Coatesville, Pa.

*Flowering habit*.—Some recurrent blooming on same panicle.

*Inflorescence dimensions*.—Up to 150 mm long and 100 mm across.

*Inflorescence quantity*.—One panicle occurring at the end of every lateral branch.

*Quantity of flowers per inflorescence*.—20 to 100 florets per panicle.

*Primary peduncle*.—Attitude/aspect — 0 degrees to the lateral branch; that is, the primary peduncle, as described herein, is the terminal portion on the lateral branch. Dimensions — 95 mm long and 3.0 mm in diameter at the base. Color — A mixture of greyed-red, RHS 178A, and greyed-orange, RHS 176A. Texture and luster of lateral branches — Glabrous, and matte. Strength — Strong.

*Secondary peduncles*.—Attitude/aspect — At an angle of approximately 30 to 45 degrees to the primary peduncle. Dimensions — 23 mm long and 1.5 mm in diameter. Color — A mixture of greyed-red, RHS 178A, and greyed-orange, RHS 176A. Texture and luster — Finely pubescent and matte. Strength — Moderately strong.

*Pedicels*.—Attitude/aspect — At an angle of approximately 30 degrees to the secondary peduncle. Dimensions — 5 mm long and 0.75 mm in diameter. Color — Yellow-green, RHS 144D, and suffused with greyed-red, RHS 178A. Texture and luster — Smooth, glabrous and matte. Strength — Moderately strong.

Flower buds:

*Bud shape*.—Globose.

*Bud dimensions*.—6 to 7 mm long and 5.5 to 6.5 mm in diameter.

*Bud color*.—Yellow-green, RHS 144D, and heavily suffused with greyed-red, RHS 178A.

Flower:

*Flower type*.—Perfect.

*Flower shape*.—Rotate.

*Persistence*.—Not persistent.

*Flower aspect*.—Outward facing.

*Fragrance*.—Not fragrant.

*Perianth dimensions*.—3.0 cm in diameter and 2.0 cm tall.

*Calyx*.—Calyx shape — Campanulate. Calyx dimensions — 6 to 7 mm in diameter and 5.5 to 6.5 mm deep. Sepals — Sepal arrangement — Rotate; fused at the base with 6 ovate sepal lobes. Number of sepal lobes — 6. Sepal lobe margins — Entire; not undulated. Sepal lobe apex — Acute. Sepal base — Fused. Sepal texture — Smooth; glabrous. Sepal color, upper surface — Yellow-green, RHS 144D, and lightly suffused with greyed-red, RHS 178A. Sepal color, lower surface — Yellow-green, RHS 144D, and lightly suffused with greyed-red, RHS 178A.

*Corolla*.—Petal arrangement — Rotate; petals arranged in a single whorl. Petal quantity — 6. Petals fused or unfused — Unfused. Petal dimensions — Approximately 15 to 20 mm long and 15 mm wide. Petal shape — Ovate. Petal apex — Rounded. Petal base — Sagittate. Petal margin — Crenate; highly undulated. Petal texture — Glabrous. Petal luster — Matte to satiny. Petal color when opening (upper side) — Red, a mixture of RHS 54C to 54D. Petal color when opening (under side) — Red, nearest to RHS 54D. Petal color when fully opened (upper side) — Red, nearest to RHS 54B. Petal color when fully opened (under side) — Red, nearest to RHS 54B. Petal color fading to — Not fading.

Reproductive organs:

*Androecium*.—Stamen quantity — 23. Filament — Dimensions — Approximately 4 mm long and approximately 0.25 mm in diameter. Color — Red, near RHS 36D, and suffused with red, RHS 55B. Anther — Anther attachment — Dorsifixed. Anther shape — Oblong. Anther size — 1.0 to 1.25 mm long and 0.75 mm in diameter. Anther color — Yellow, RHS 13B. Pollen — Amount of pollen — Moderately abundant. Pollen color — Yellow, RHS 13B.

*Gynoecium*.—Pistil quantity — One. Stigma — Shape — Round. Dimensions — Approximately 0.75 mm across and 0.75 mm tall. Color — Yellow-green, RHS 144C. Style — Dimensions — 5 mm long and 0.5 mm in diameter. Color — Yellow-green, RHS 144C. Ovary — Position — Superior. Shape — Globose. Diameter — 2 mm. Color — Yellow-green, RHS 144C.

Seed and fruit: Globose, six-valved dehiscent capsule which is approximately 6 mm in diameter and 6 mm long; color is yellow-green, RHS 144B, and maturing to brown, RHS 200C. Seed has not been observed.

COMPARISON WITH THE PARENT PLANT

Plants of the new cultivar 'Lipipetz' may be distinguished from its parent, *Lagerstroemia* 'Hopi' (not patented), which is also the most similar known commercial comparator, by the characteristics described in Table 1.

TABLE 1

| Characteristic | 'Lipipetz' | 'Hopi' |
|---|---|---|
| Mature plant size. | Smaller than 'Hopi'. | Larger than 'Lipipetz'. |
| Internode length along the main stem. | Approximately .25 to 2.5 cm. | Approximately 5 to 10 cm. |
| Leaf size. | Leaves are smaller. | Leaves are larger. |
| Rate of maturity of the lateral branches. | Lateral branches become woody by late summer. | Softwood is still present into early fall. |
| Lateral branch hardiness. | More hardy than 'Hopi'. | Less hardy than 'Lipipetz'. |

COMPARISON WITH THE CLOSEST KNOWN COMMERCIAL COMPARATOR

Plants of the new cultivar 'Lipipetz' are similar in growth habit to the commercial variety, *Lagerstroemia* 'Velma's Royal Delight' (not patented). However, 'Lipipetz' differs from 'Velma's Royal Delight' by the characteristics described in Table 2.

TABLE 2

| Characteristic | 'Lipipetz' | 'Velma's Royal Delight' |
|---|---|---|
| Mature plant size. | Approximately 125 cm tall and 125 cm wide. | Upwards of 180 to 250 cm tall and 180 cm wide. |
| General coloration of the flower. | Pink. | Deep magenta. |
| Lateral branch hardiness. | More hardy than 'Hopi'. | Less hardy than 'Lipipetz'. |

That which is claimed is:

1. A new and distinct cultivar of *Lagerstroemia* plant named 'Lipipetz', substantially as described and illustrated herein.

* * * * *